United States Patent [19]

McLeod

[11] Patent Number: 5,877,171
[45] Date of Patent: Mar. 2, 1999

[54] METHOD OF TREATING PRE-MENSTRUAL SYNDROME USING CHROMIUM

[76] Inventor: Malcolm N. McLeod, 419 Lakeshore La., Chapel Hill, N.C. 27514

[21] Appl. No.: 901,841

[22] Filed: Jul. 28, 1997

[51] Int. Cl.⁶ .......................... A61K 31/555; A61K 32/24
[52] U.S. Cl. ........................ 514/188; 424/655; 514/321; 514/505; 514/640; 514/647; 514/654; 514/899
[58] Field of Search ...................................... 514/505, 188

[56] References Cited

U.S. PATENT DOCUMENTS

| 5,196,351 | 3/1993 | Harris et al. | 436/501 |
| 5,422,281 | 6/1995 | Harris et al. | 436/501 |
| 5,470,846 | 11/1995 | Sandyk | 514/159 |

OTHER PUBLICATIONS

Sue Miller, "A Natural Mood Booster", *Newsweek,* (May 5, 1997), 74–75.

Liu et al., "Biphasic Effects of Chromium Compounds on Catecholamine Secretion from Bovine Adrenal Medullary Cells", *Toxicology,* vol. 117 (1997), 45–53.
Chemical Abstracts vol. 114:221161c Stone et al, 1991.
Chemical Abstracts vol. 122: 299110v Choay et al, 1995.
Chemical Abstracts vol. 125: 67810g Oguiza et al, 1996.

*Primary Examiner*—Leonard Schenkman
*Attorney, Agent, or Firm*—Jenkins & Wilson, P.A.

[57] ABSTRACT

The method of this invention is directed to a treatment of depression in men and women and to a treatment of pre-menstrual syndrome (PMS) in women by administering to a patient a therapeutically effective amount of chromium in a pharmaceutically acceptable form either alone or in conjunction with the administration of a standard antidepressant composition, such as a selective serotonin reuptake inhibitor composition. Chromium, preferably in the form of chromium picolinate, is administered to the patient at dosages in a preferred range of about 200 to about 500 micrograms chromium.

12 Claims, 7 Drawing Sheets

5,877,171

METHOD OF TREATING PRE-MENSTRUAL SYNDROME USING CHROMIUM

TECHNICAL FIELD

The present invention relates generally to a treatment for depression and to a treatment of pre-menstrual syndrome, and more particularly to the treatment of depression using chromium and to the treatment of pre-menstrual syndrome using chromium. The present invention also particularly relates a method of improving the effectiveness of an antidepressant composition by administering chromium to a patient concurrently with the administration of an antidepressant composition to the patient.

BACKGROUND ART

It will be appreciated by those having ordinary skill in the art that depression is a difficult mental disorder to treat. Patients having such a disorder are often reluctant to seek the medical attention necessary to diagnose the disorder. Such reluctance is often related to the patient's fear of the stigma associated with seeking psychiatric help or to the patient's feelings of worthlessness associated with depression. Moreover, once patients seek competent psychiatric help, it is difficult to successfully treat the disorder through psychoanalytic approaches alone.

In the *Diagnostic and Statistical Manual of Mental Disorders,* Fourth Edition, (DSM IV) published by the American Psychiatric Association, depressive disorders are classified under mood disorders and are divided into three types: major depressive disorder, dysthymic disorder and depressive disorder not otherwise specified. Major depressive disorder and dysthymic disorder are differentiated based on chronicity, severity and persistence. In major depression the depressed mood must be present for two weeks. In dysthymic disorder the depressed mood must be present most days over a period of two (2) years. Usually major depressive disorder is characterized by its sharp contrast to usual functioning. A person with a major depressive episode can be functioning and feeling normally and suddenly develop severe symptoms of depression. By contrast a person with dysthymic disorder has chronic depression with less severe symptoms than major depression.

In an effort to treat depression, a variety of antidepressant compositions have been developed. Among these are the selective serotonin reuptake inhibitors (SSRI), such as sertraline (registered trademark ZOLOFT® - Pfizer), fluoxetine (registered trademark PROZAC® - Eli Lilly), paroxetine (trade name PAXIL™ - Smith Kline Beecham) and fluvoxamine (trade name LUVOX™). Other examples of antidepressant compositions include tricyclic antidepressants such as that sold under the registered trademark ELAVIL® (Merck, Sharpe and Dohme), aminoketone antidepressants such as bupropion, and lithium, a metal used to treat bipolar disorder. However, these drugs are very potent, often generating problematic side effects such as lethargy, clouded thinking and a lack of ability to concentrate.

Fluoxetine is also known to be efficacious in the treatment of dysmenorrhea and pre-menstrual syndrome (PMS). Steiner et al., New England Journal of Medicine 332:1529–34 (1995). The symptoms of PMS include dysphoria, craving for carbohydrates, exhaustion, muscle aches and cramps, among others. A detailed description of the symptoms of PMS can be found in the *Diagnostic and Statistical Manual of Mental Disorders,* Fourth Edition, (DSM IV) published by the American Psychiatric Association. However, approximately forty percent (40%) of women who are suffering from PMS do not have a positive response to fluoxetine when treated with it.

Chromium, in its pharmaceutically acceptable trivalent form, has been used in the treatment of overeating as it is documented to control appetite. Trivalent chromium is commercially available as chromium picolinate. Chromium has also been documented as playing a role in facilitating the action of insulin in the body. In this regard, toxicity concerns relating to chromium have been demonstrated to be quite low.

There has been no description of the use of chromium in the treatment of depression or in the treatment of pre-menstrual syndrome.

A method of treating neurological and mental disorders was described in Sandyk U.S. Pat. No. 5,470,846. However, the method of this reference includes the application to the brain of a patient of a sufficient amount of an AC pulsed magnetic field of proper intensity and frequency to treat the disorder. In conjunction with the application of the AC pulsed magnetic field, a stimulant to facilitate the transport of tryptophan into the brain is administered. Chromium, preferably in the form of chromium picolinate, is described as a stimulant. However, when the disclosure of this application of chromium is taken as a whole, the deficiencies become apparent. First of all, the application of the AC pulsed magnetic field is required in the method. Additionally, a patient, particularly in the case of depression, may be resistant to accepting such a complex treatment.

Therefore, what is needed then is an effective, pharmacologically-based treatment for depression and for pre-menstrual syndrome that potentiates the action and reduces the side effects of known compositions used in the treatment of these disorders. Such a method of treatment is lacking in the prior art.

DISCLOSURE OF THE INVENTION

The method of this invention comprises the treatment of depression by administering to a patient a therapeutically effective amount of chromium in a pharmaceutically acceptable form either alone or in conjunction with the administration of a standard antidepressant composition. The administration of the pharmaceutically acceptable form of chromium does not need to be carried out in the presence of applying a magnetic field to a patient and is desirably carried out in the absence of any such application of a magnetic field.

Any standard antidepressant composition is contemplated to be within the scope of this invention. Among these are the selective serotonin reuptake inhibitors (SSRI), such as sertraline (registered trademark ZOLOFT® - Pfizer), fluoxetine (registered trademark PROZAC® - Eli Lilly), paroxetine (trade name PAXIL™- Smith Kline Beecham) and fluvoxamine (trade name LUVOX™). Other examples include tricyclic antidepressants such as that sold under the registered trademark ELAVIL® (Merck, Sharpe and Dohme), aminoketone antidepressants such as bupropion, and lithium, a metal used to treat bipolar disorder.

Chromium is administered one to three times a day. A preferred range is about 50 to about 1,000 $\mu$g daily. A more preferred range is about 100 to about 600 $\mu$g daily. A most preferred range is about 200 to about 500 $\mu$g chromium daily. The preferred form of chromium is chromium picolinate.

Stated differently, a preferred range is about 1 $\mu$g to about 10 $\mu$g chromium per kilogram body weight of the patient daily. A more preferred range is about 2 $\mu$g to about 8 $\mu$g chromium per kilogram body weight of the patient daily. A most preferred range is about 4.5 μg to about 6 μg chromium per kilogram body weight of the patient daily.

Also, contemplated to be within the scope of this invention are a method of treating dysmenorrhea, a method of treating pre-menstrual syndrome, and a method of treating alcoholism. These methods comprise the administration of a therapeutically effective amount of chromium in a pharmaceutically acceptable form to a patient in need thereof. Similar dosage ranges as those presented above are applicable to these methods.

Accordingly, it is an object of this invention to provide a method of treating depression that is pharmacologically-based.

It is a further object of this invention to provide a method of treating depression that is more appealing to patients.

It is yet a further object of this invention to provide a method for improving the effectiveness of anti-depressant compositions.

It is yet another object of this invention to provide a method of treating alcoholism.

It is still another object of this invention to provide a method of treating pre-menstrual syndrome (PMS).

Some of the objects of the invention having been stated hereinabove, other objects will become evident as the description proceeds, when taken in connection with the accompanying drawings as best described hereinbelow.

DETAILED DESCRIPTION OF THE INVENTION

Figure 1:
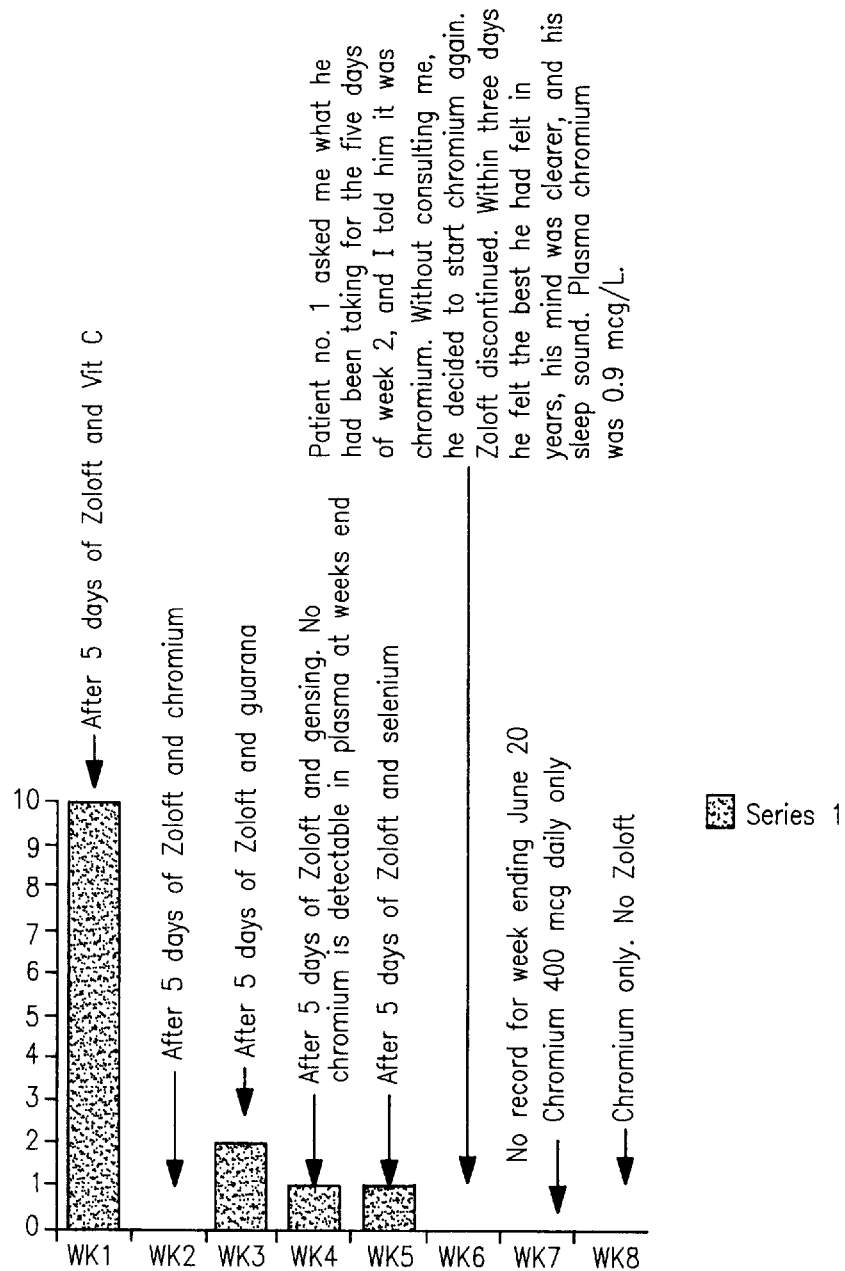
FIG. 1 is a graphical representation of the Beck Scale data from Patient No. 1 in Example 1.

As noted above, there are three types of depression generally characterized in the art, major depression, dysthymic disorder, or dysthymia, and depressive disorder not otherwise specified. Major depression is characterized by peak episodes of extreme depression. During a peak episode, the patient may suffer from dysphoria, craving for carbohydrates, exhaustion, muscle aches, and dangerously suicidal notions.

Dysthymia is characterized by chronic low moods that can last for long periods of time in the life of the patient, such as 20 years. Dysthymia is further characterized by lack of passion for things in the sufferer's life, including work, food, and/or sexual relations, and by dysphoria.

Diagnosis criteria for dysthymia and major depression are more fully explained in the *Diagnostic and Statistical Manual of Mental Disorders,* Fourth Edition, (DSM IV) published by the American Psychiatric Association, the contents of which are herein incorporated by reference.

The method of this invention comprises the treatment of depression by administering to a patient a therapeutically effective amount of chromium in a pharmaceutically acceptable form either alone or in conjunction with the administration of a standard antidepressant composition. The administration of the pharmaceutically acceptable form of chromium does not need to be carried out in the presence of applying a magnetic field to a patient and is desirably carried out in the absence of any such application of a magnetic field.

In the methods of the instant invention, chromium is administered one to three times a day. The preferred form of chromium, chromium picolinate, is commercially available. An acceptable source is marketed under the trademark Nature Made®. From this source each tablet contains 200 μg chromium from chromium picolinate. The tablets from this source also include dibasic calcium phosphate, cellulose and magnesium stearate. A daily nutritional value from chromium is yet to be established.

Thus, a preferred dosage range for chromium is about 50 to about 1,000 μg daily. A more preferred range is about 100 to about 600 μg daily. A most preferred range is about 200 to about 500 μg chromium daily. The preferred form of chromium is chromium picolinate.

Stated differently, a preferred range is about 1 μg to about 10 μg chromium per kilogram body weight of the patient daily. A more preferred range is about 2 μg to about 8 μg chromium per kilogram body weight of the patient daily.

Most preferred dosage ranges of chromium are those doses sufficient to deliver from about 4.5 to about 6 μg of chromium per kilogram (kg) of body weight. This dosage range is generally several fold greater than that contained in most commercially available multi-vitamin and mineral preparations. This amount results in a plasma chromium level between 0.9 μg/liter to 2.1 μg/liter. The plasma level will vary depending on the level of exercise, i.e., the more one exercises, the more chromium is required to maintain plasma levels.

To more fully characterize dosage information, the most preferred dosage range is calculated based on consuming enough chromium picolinate to deliver about 200 to about 500 μg elemental chromium. According to standard stoichiometric calculations, in delivering 200 μg elemental chromium, approximately 1600 μg chromium picolinate is consumed in a standard commercial preparation.

It is also preferable to take the last, or only, daily dose of chromium eight (8) hours prior to sleep to avoid insomnia. It is also noted that diabetics and hypoglycemics should use chromium only under a physician's supervision.

Commercially available tubes for the collection of blood can contain significant amounts of chromium. To avoid contamination, plasma levels of chromium should be determined from blood collected in heparinized or EDTA tubes.

Also, contemplated to be within the scope of this invention are a method of treating dysmenorrhea (painful menses), a method of treating pre-menstrual syndrome (PMS), and a method of treating alcoholism or alcohol craving. These methods comprise the administration of a therapeutically effective amount of chromium in a pharmaceutically acceptable form to a patient in need thereof. Similar dosage ranges as those presented above are applicable to these methods.

Any standard antidepressant composition is contemplated to be within the scope of this invention. Among these are the selective serotonin reuptake inhibitors (SSRI), such as sertraline (registered trademark ZOLOFT® - Pfizer), fluoxetine (registered trademark PROZAC® - Eli Lilly), paroxetine (trade name PAXIL™- Smith Kline Beecham) and fluvoxamine (trade name LUVOX™). Other examples include tricyclic antidepressants such as that sold under the registered trademark ELAVIL® (Merck, Sharpe and Dohme), aminoketone antidepressants such as bupropion, and lithium, a metal used to treat bipolar disorder.

In the foregoing examples, chromium picolinate is preferred source of chromium. Other acceptable sources include chromium citrate, chromium chloride and chromium acetate. Other pharmaceutically acceptable forms of chromium would be apparent to one having ordinary skill in the art.

The following examples are set forth to illustrate the subject invention. The examples should not be considered as limiting, the scope of the invention being defined by the claims appended hereto.

EXAMPLE 1

Treatment of Dysthymia

Patient No. 1 was a 50-year old white male who, after a series of psychoanalysis/psychotherapy sessions, was diagnosed as suffering from depression in the form of dysthymia. Patient No. 1 experienced a chronic low mood with markedly diminished interest and pleasure in all activities including work, eating, and sexual relations.

Initially, Patient No. 1 was treated only with the known antidepressant sertraline (sold under the registered trademark ZOLOFT®). Sertraline is a selective serotonin reuptake inhibitor. Sertraline was administered in amounts from 50 to 150 mg qd(per day); and it was ultimately determined that the ideal dose for this patient was 125 mg qd (per day). Sertraline provided some relief of the symptoms of dysthymia; but, often made the patient sluggish in his daily activities and made his thinking cloudy, or fuzzy.

Independent of the sertraline treatments, the patient began taking a vitamin and mineral supplement that included a series of components. While taking this vitamin and mineral supplement, the patient noticed a marked improvement in his condition. As such improvement was unexpected, a study of the components of the mineral preparation was undertaken. During this study Patient No. 1 stopped taking the composite preparation.

In this study, Patient No. 1 took one component of the preparation at a time according to a schedule of one pill a day for five days, Monday through Friday. At the end of each week, he filled out two self-rating scales that are used in the diagnosis and monitoring of depression. These scales are the Beck Scale and the SCL-90 Scale, both of which are well known in the field of psychiatry and psychotherapy. Patient No. 1 continued to take sertraline at 125 mg per day. During the study, Patient No. 1 was not informed of what he was taking.

During the week prior to the beginning of the study, Patient No. 1 took sertraline at 125 mg qd alone. He experienced loss of energy, disturbed sleep, and awaking tired. He also experienced a loss of muscle strength when exercising, muscle tightness in the neck and shoulders, hard bowel movements, frequent mild headaches, ringing in the ears (which has worsened since starting the sertraline), lack of focus on any activities, and loss of desire for sex. No Beck Scale or SCL-90 Scale was given prior to this period.

During the first week of the study, Patient No. 1 received a placebo of vitamin C along with the 125 mg of sertraline each day for five days. His condition continued to worsen. His thought processes were cloudy, and he had trouble concentrating which interfered with his work. During a meeting at his work, he had trouble following the discussions. As demonstrated in the graph in FIG. 1, his total Beck score was +10, indicating a depressed condition.

During the second week, Patient No. 1 received chromium in the form of chromium picolinate. Patient No. 1 took 200 µg of chromium from chromium picolinate per day along with 125 mg of sertraline. He noticed a dramatic, certain and immediate relief of symptoms. He observed an increase in energy and his appetite was under control. His appearance was relaxed and cheerful, as observed by the inventor in a meeting approximately three days after Patient No. 1 began to take chromium. The total Beck score at the end of the week was 0, indicating no depression.

During the third week, Patient No. 1 took 125 mg of sertraline qd. and one guarana pill each day. Guarana was selected as the next component because it contains caffeine. During this week, he became dehydrated, had a slight headache and sore muscles, suffered from disturbed sleep and loss of energy, and his carbohydrate craving returned. He noted that he felt like he had taken too much caffeine. The Beck score at the end of this week was a +2.

During the fourth week, Patient No. 1 took 125 mg sertraline qd and ginseng. Patient No. 1 observed that this week was better than last week, but not as good as the week before. He felt low on energy and dehydrated. At the end of this week, no chromium was detectable in his plasma. His Beck score was also +1.

During the fifth week, Patient No. 1 took selenium and sertraline 125 mg qd. During this week, he felt agitated, as when he had consumed too much caffeine. He also did not feel rested when he awoke from sleep.

At this point, the study was ceased. The patient inquired as to what he was taking during week 2 and was informed that he was taking chromium picolinate. On his own initiative, he consumed 400 µg of chromium picolinate and immediately felt much better. Patient No. 1 then continued to take 400 µg of chromium of chromium picolinate per day (200 µg twice daily or b.i.d.). Further, the patient discontinued the sertraline treatment to further characterize the relationship between chromium and sertraline. During this week, the patient noted that his sleep was much improved, that his mind was clearer than when he was taking sertraline, that he did not crave food or alcohol, and that for the first time in years he was hopeful about the future. At this point in the study, his plasma chromium level was 0.9 µg/L.

For Patient No. 1, a potential adverse side effect was observed. The patient reported that after taking 200 µg of chromium from chromium picolinate late in the day, his sleep was disturbed. He therefore decided to take it no later than 3:00 p.m. He then reported that he slept much better after taking the second dose of chromium picolinate earlier in the day.

The patient's progress was tracked over an additional six-week period. The patient stated that he had felt the best he had felt in a decade. He characterized himself as feeling good mentally and physically. He stated that he began to feel normal. He felt better when taking the chromium picolinate alone than when taking chromium picolinate and sertraline at the same time. The patient stated that he felt a "a bit slowed down" and his thinking was dulled when he taking sertraline in addition to the chromium picolinate.

Patient No. 1 further observed that during a crisis period at work during the last week of the study described herein, he increased his chromium from chromium picolinate intake to 200 µg t.i.d., or three times daily. Within an hour, he noticed immediate improvement and was able to deal with his crisis.

Figure 2:
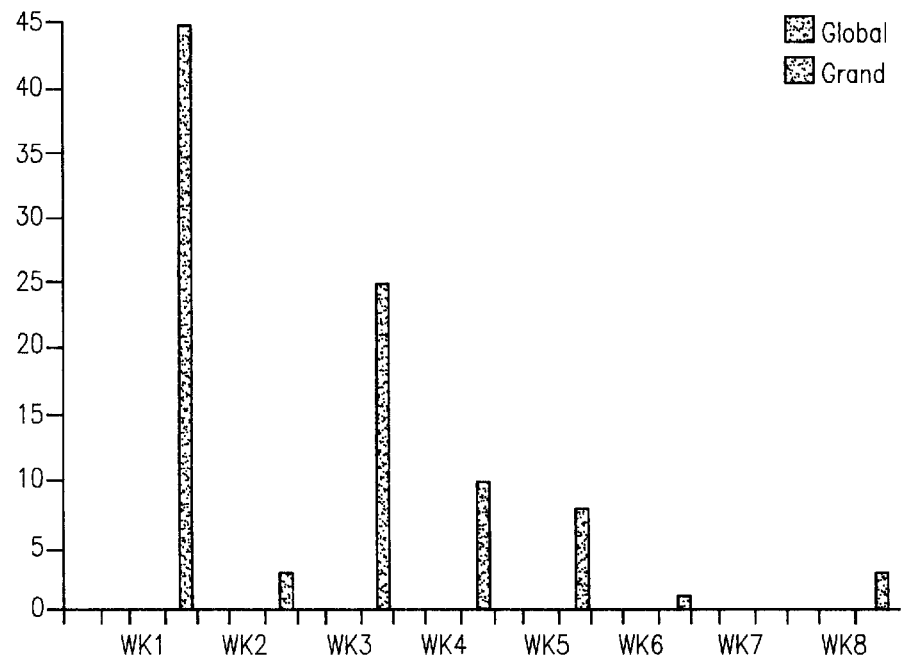
FIG. 2 is a graphical representation of SCL-90 Scale data from Patient No. 1 in Example 1.

The series of events described in the above example are more fully set forth in the graphs in FIGS. 1 and 2. FIG. 1 is a bar graph displaying the scores on the Beck Scale, a self-rating scale for depression, at the end of each weekly treatment.

FIG. 2 is a bar graph of the total score on the SCL-90 Scale. The SCL-90 is composed of 90 questions. It is designed to measure symptoms of somatization, obsessive-compulsive behavior, interpersonal sensitivity, depression, anxiety, hostility, phobic anxiety, paranoid ideation, and psychoticism. It is noted that the grand total of scores on each Friday closely parallels the results of the Beck Scale.

Figure 3:
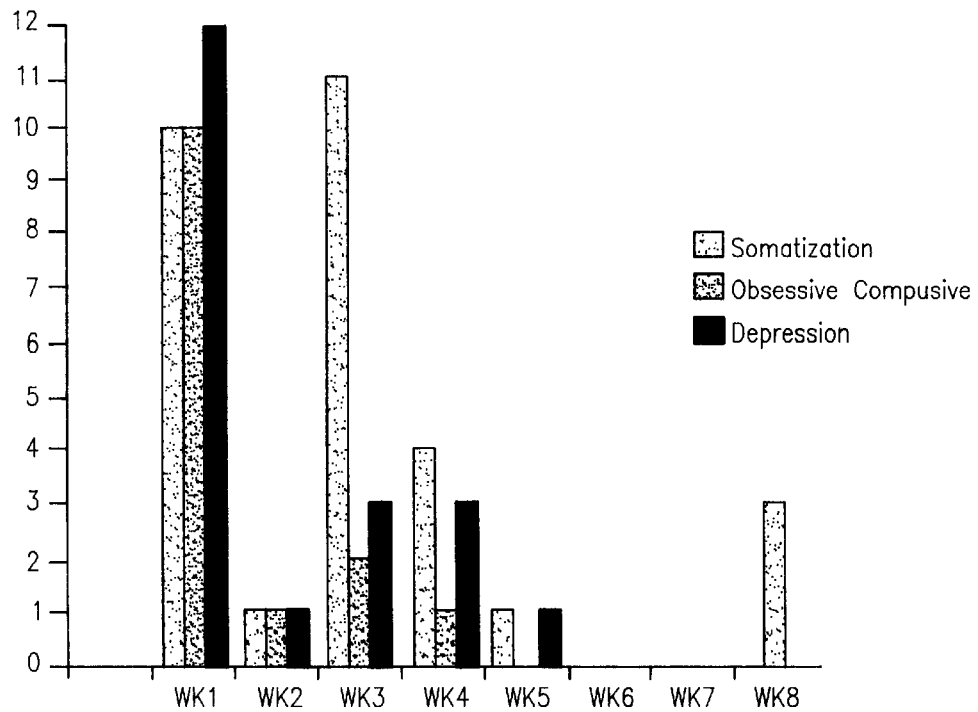
FIG. 3 is a graphical representation of the SCL-90 Sub-scale data for Patient No. 1 in Example 1.
Figure 4:
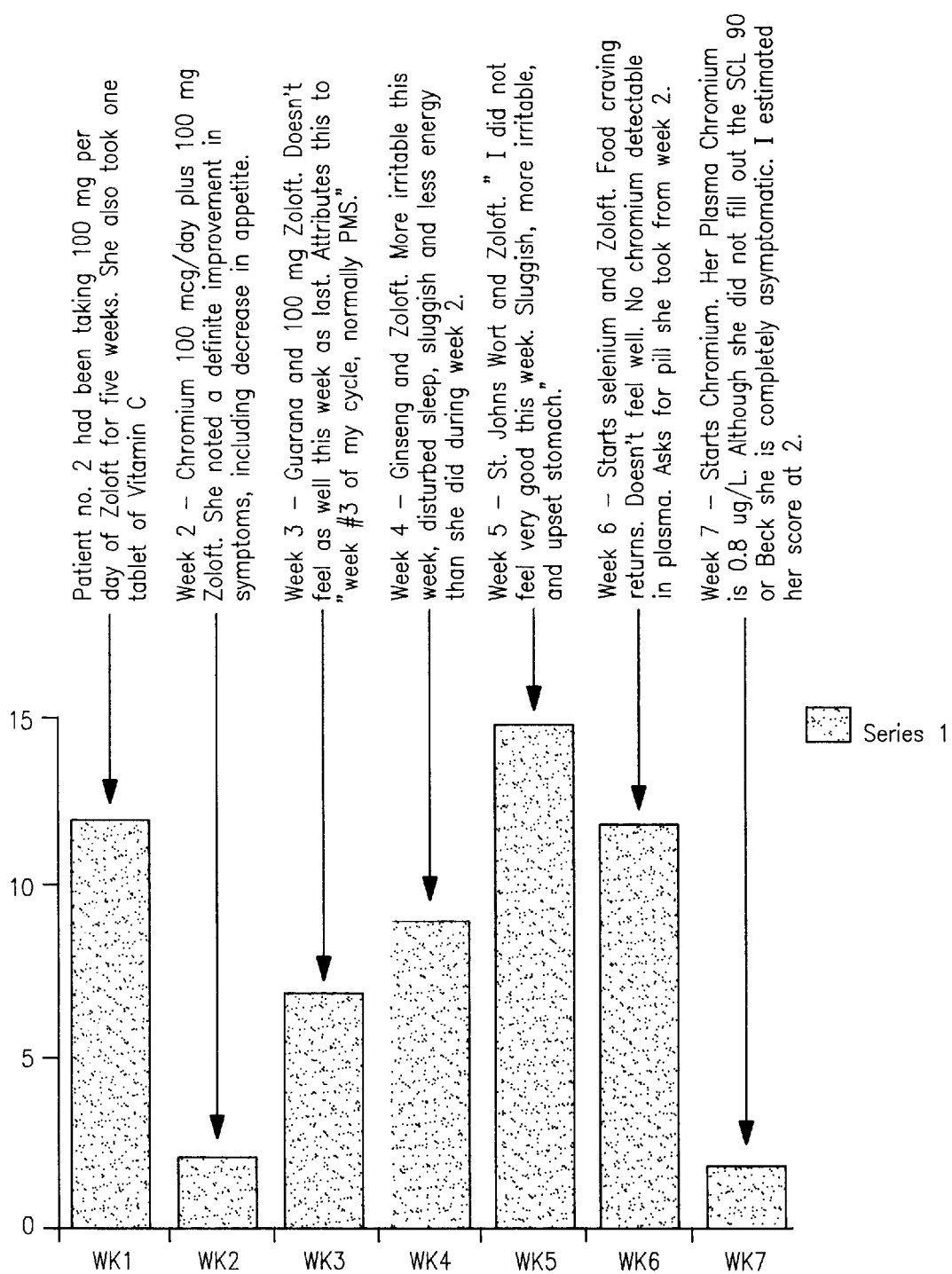
FIG. 4 is a graphical representation of the Beck Scale data for Patient No. 2 in Example 2.

FIG. 3 is a graph of three subscales of the SCL-90 (somatization, obsessive-compulsive, and depression). These subscales reflect the greatest changes. The marked elevation on the somatization scale during the week after chromium picolinate was stopped may have been due to the caffeine effect of guarana and/or lack of chromium picolinate. It is noted that the positive reading during the last week of the therapy was due to Patient No. 1 experiencing certain unpleasant and unwanted thoughts regarding the crisis at his work referenced above. There was no return of somatic symptoms of depression.

Treatment of alcoholism or alcohol craving

During the later stages of the study described above, when Patient No. 1 was taking chromium picolinate alone, he also noticed a change in his ability to tolerate alcohol. Both of his parents were alcoholics so he guarded carefully against this outcome by drinking infrequently.

Despite this effort, he often experienced intense cravings for alcohol. Prior to his treatment with chromium, when he consumed alcohol, he could only drink it by gulping it. He experienced rapid intoxication, unpleasant feelings, and a severe hangover the next day. Since treatment with chromium picolinate began as described above, he observed significantly diminished alcohol cravings. He also observed that he could drink in moderation, without having a severe hangover the next day.

Thus, a method of treating alcoholism or alcohol cravings is contemplated to be within the scope of this invention.

EXAMPLE 2

Treatment of Dysthymia

Patient No. 2 was a 25-year old single white female. She is the daughter of Patient No. 1. She complained of weight gain, hyperphagia, hypersomnia, loss of interest in sex, irritability and an inability to concentrate. She stated that she had been seeing psychotherapists since she was 13 years old, but had no success in dealing with her depression. She was also diagnosed as having dysthymia.

She had taken sertraline in the amount of 50 mg qd. with little help. This dosage was increased to 100 mg qd. which proceeded for a period of five weeks. She was still symptomatic of depression, but felt better. She was not as weepy and her outlook was less negative. Her interest in sex was increased. Her appetite remained the same. The sertraline treatment improved her interest in a former hobby, reading.

Patient No. 2 then began a similar study as that described above for Patient No. 1. For the first week, she took one vitamin C tablet daily along with 100 mg of sertraline. Her depression appeared to worsen as reflected by her grand total Beck score of +12 and her SCL-90 +4 as more fully portrayed on the FIG. 5. She suggested that it was more difficult to more accurately evaluate women because of PMS.

During the second week, Patient No. 2 started 200 µg of chromium from chromium picolinate per day and continued 100 mg sertraline per day. Her SCL-90 score demonstrated a definite improvement. She wrote on her Beck Scale that her appetite was less.

For week three she took guarana and continued sertraline at 100 mg per day. She noted that she did not feel as well during this week as the previous week. Week three was also the start of her menstrual cycle in which she normally experienced PMS.

During the fourth week she took ginseng and continued sertraline at 100 mg per day. During the middle of this week she complained of low energy, headache, restlessness, and initial insomnia. She stated that she definitely had less energy than week two when she was taking chromium picolinate.

During week five she began taking St. John's Wort, a herb believed to have antidepressant effects. She also continued sertraline at 100 mg per day. No positive response was observed.

During week six she began taking selenium and continued 100 mg sertraline per day. Her food craving returned and she generally did not feel well. At this point, Patient No. 2 became impatient with this study and wished to resume taking the medication that was effective. She therefore discontinued taking selenium and began taking chromium picolinate at 200 µg per day beginning the Monday of the next week.

Within two days she felt better and had no symptoms. She considered the study over and therefore did not take either the Beck Scale of the SCL-90. It was estimated via a telephone interview that her Beck Scale was +2. Four days following her resuming treatment with chromium picolinate her plasma chromium was 0.8 µg/L.

Patient No. 2 continued to take sertraline along with chromium picolinate because of a stressful situation at her workplace. Despite this added stress at work, she noted that she was able to function much better than in the past. She stated that things just did not seem to bother her as much as they used to bother her.

Treatment of Pre-menstrual Syndrome (PMS)

While Patient No. 2 was taking chromium picolinate according to the dosages described above, she further observed that her menses was less problematic. She said that she had less carbohydrate craving during the week before, that she was less irritable, that her dysphoria was relieved, and that her usual cramps were non-existent. Thus, an aspect of the present invention includes the treatment of pre-menstrual syndrome (PMS), or dysmenorrhea (problematic and/or painful menses), comprising administering chromium in a preferred dose of 200 µg per day to a patient in need thereof.

Figure 5:
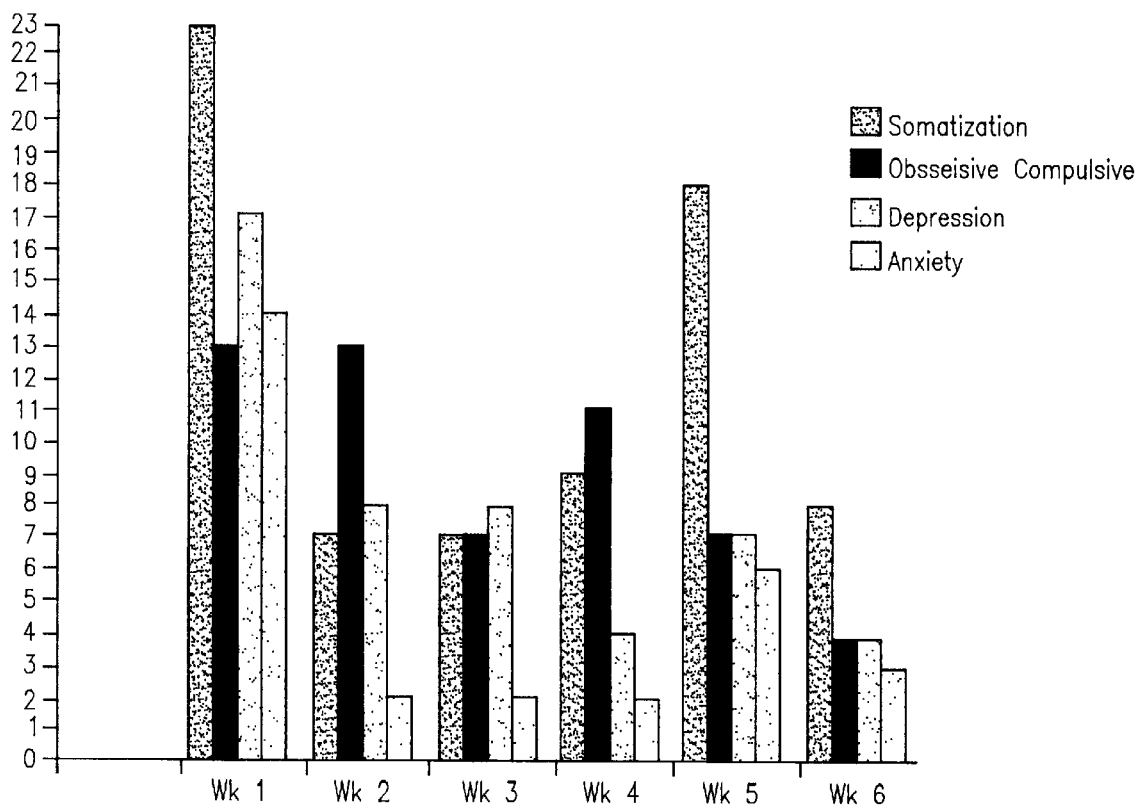
FIG. 5 is a graphical representation of the SCL-90 Sub-scale data from Patient No. 2 in Example 2.
Figure 6:
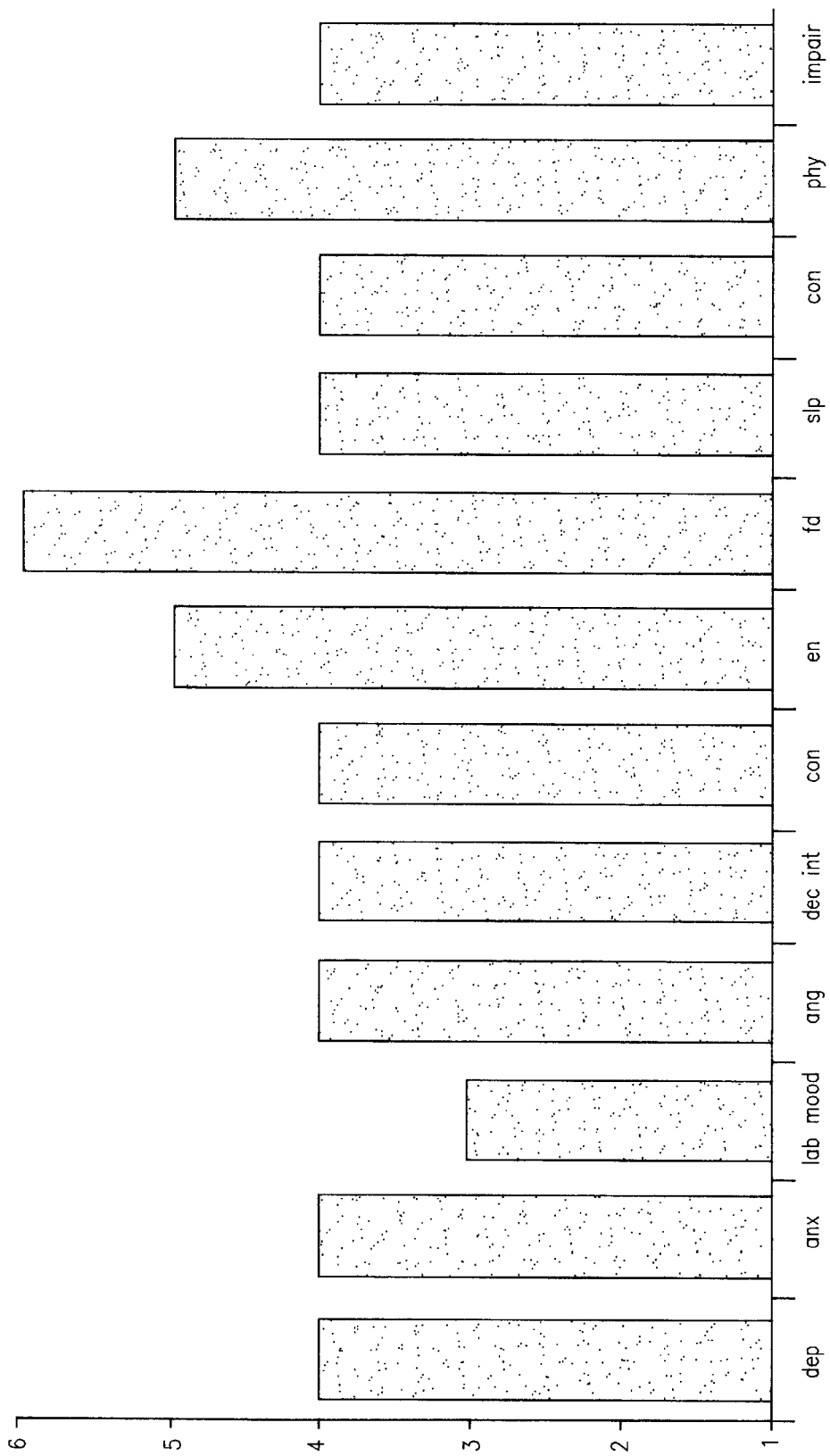
FIG. 6 is a graphical representation of the severity of the symptoms of pre-menstrual syndrome as experienced by Patient No. 4 when taking paroxetine and lithium.

For Patient No. 2, FIG. 5 presents Patient No. 2's Beck Scale total scores, and FIG. 6 presents a graph of the four subscales of somatization, obsessive-compulsive, depression, anxiety on the SCL-90 Scale.

EXAMPLE 3

Treatment of Severe Dysthymia

Patient No. 3 was a 42-year old divorced man experiencing chronic suicidal depression for about 15 years. For as long as the patient can remember, he has had episodic, mild-to-moderate mood swings. Approximately 15 years ago his condition worsened and he was depressed almost daily. His thoughts were slowed down, he felt intensely sad, guilty, worthless, confused, and desperate. Over a period of approximately two years he underwent therapy with a social worker and psychotherapy with a psychiatrist, with little positive results. No pharmacotherapy was involved in either of these treatments.

Initially, Patient No. 3 met with the inventor and identified a childhood source as a partial cause of his depression, low self-esteem and dysfunctional thinking. Although he appreciated the insights gained through the psychoanalysis/psychotherapy with the inventor, his depression persisted unabated. He was rejected by his girlfriend and became frighteningly suicidal.

Approximately eight months prior to the beginning of the treatment as described below, he began taking 50 mg of ELAVIL® (a registered trademark for Merck, Sharpe and Dohme for the antidepressant, amitryptline HCl, a tricyclic antidepressant) per day which helped him sleep and allowed him, in his words, to think more rationally. Within six months he developed a tolerance to the drug and it was increased to 100 mg per day with no effect. He stopped ELAVIL® and started bupropion 100 mg b.i.d and lithium 300 mg t.i.d. Bupropion is an aminoketone antidepressant, and lithium is a metal used to treat bipolar disorder.

The bupropion treatment was discontinued because he developed involuntary muscle twitches. His condition was desperate and life-threatening. He was therefore prescribed sertraline at 100 mg qd and was given 12 200 μg pills of chromium picolinate with instructions to take one pill b.i.d., or twice daily.

Patient No. 3 observed that after four to five days there was a perceptible change in his mood. He stated that he felt close to contentment and might be there soon.

Thus, another aspect of this invention is that administration of chromium in conjunction with the administration of a selective serotonin reuptake inhibitor (SSRI) like sertraline reduces the delay in the lag time normally associated with an SSRI. Stated differently, there is lag time of normally 30 days before the SSRI's effect on depression is noted. In this case, Patient No. 3 experienced relief of symptoms within four to five days.

Two to three days after he took the last chromium picolinate tablets he began to feel as if he were slipping back and began feeling sad and pessimistic. He was then given a three-week supply of chromium picolinate so that he could take one pill providing 200 μg of chromium from chromium picolinate twice daily. Within a matter of days, Patient No. 3 noted that he rebounded and felt better than he had felt in many years.

He further observed that he felt like himself again and that he felt content in many ways. He stated that he had gained control of his life that he had felt deprived of for so long. He noted that instead of obsessing for many hours over his low mood and past mistakes, he was able to focus on practical matters. He became optimistic about his future and about his artistic endeavors. He also felt as if his mind was becoming unburdened of much of the negative clutter that kept him from dealing with his problems.

While taking chromium picolinate, Patient No. 3 was again rejected by his girlfriend. Rather than slipping again into depression, he accepted this in stride and continued with his life.

Therefore, Patient No. 3, a patient suffering from severe dysthymia, noticed marked improvement after taking chromium picolinate in a preferred dosage providing chromium in the amount of 200 μg twice daily, or 400 μg per day.

EXAMPLE 4

Treatment of Major Depression, Dysphoria and Pre-Menstrual Syndrome

Patient No. 4 was a 45-year old woman who has struggled to overcome a wide variety of psychiatric symptoms, two of which are depression and pre-menstrual syndrome (PMS). After several treatments, it was determined that a combination of paroxetine 20 mg t.i.d. and lithium 300 mg t.i.d. diminished her symptoms of obsessive-compulsive disorder, depression, hypomania and PMS. While taking this combination, she rated her PMS as moderate to severe and barely tolerable. See the chart more fully set forth in FIG. 6.

Figure 7:
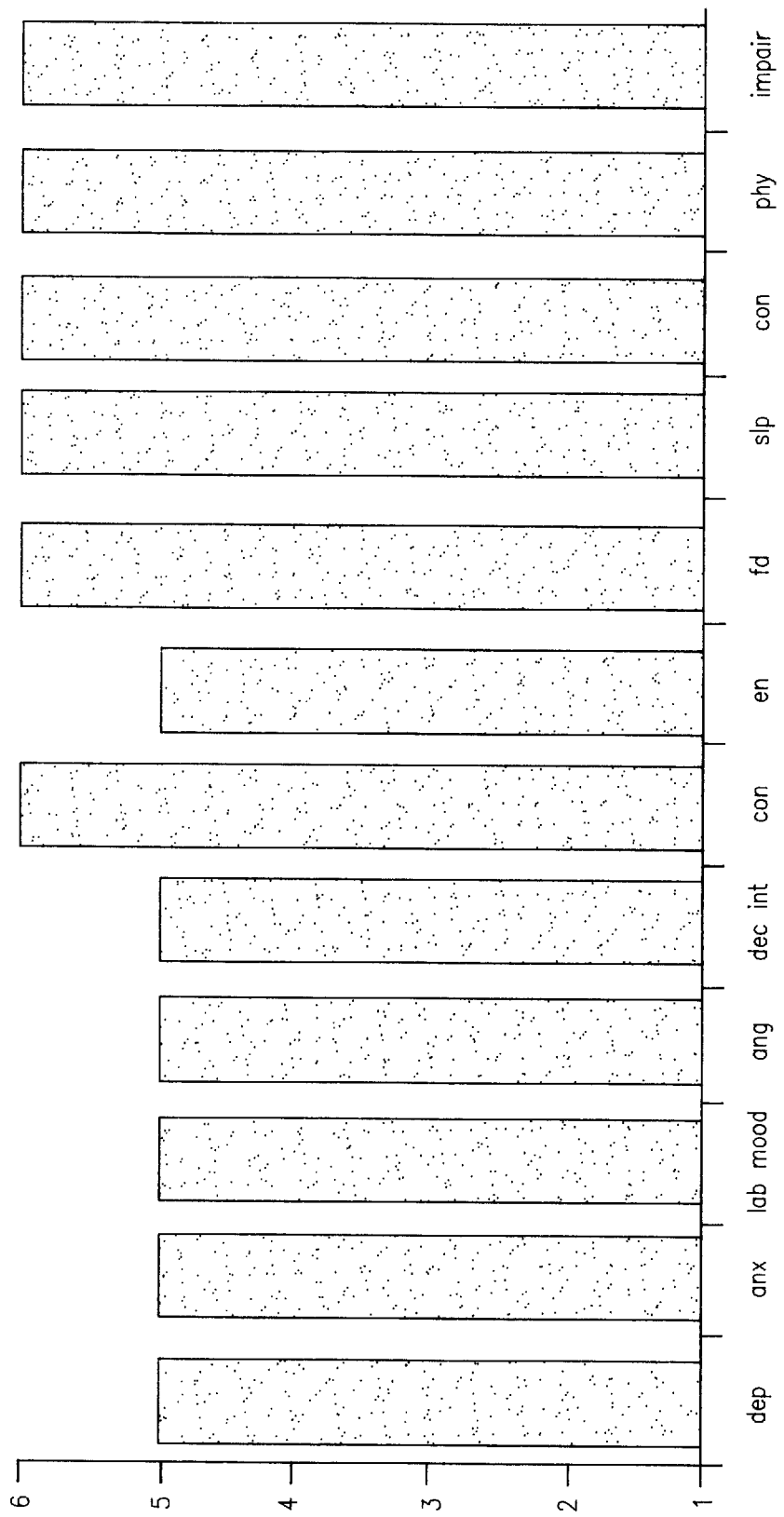
FIG. 7 is a graphical representation of the severity of the symptoms of pre-menstrual syndrome from Patient No. 4 in Example 4 when taking no medication.
Figure 8:
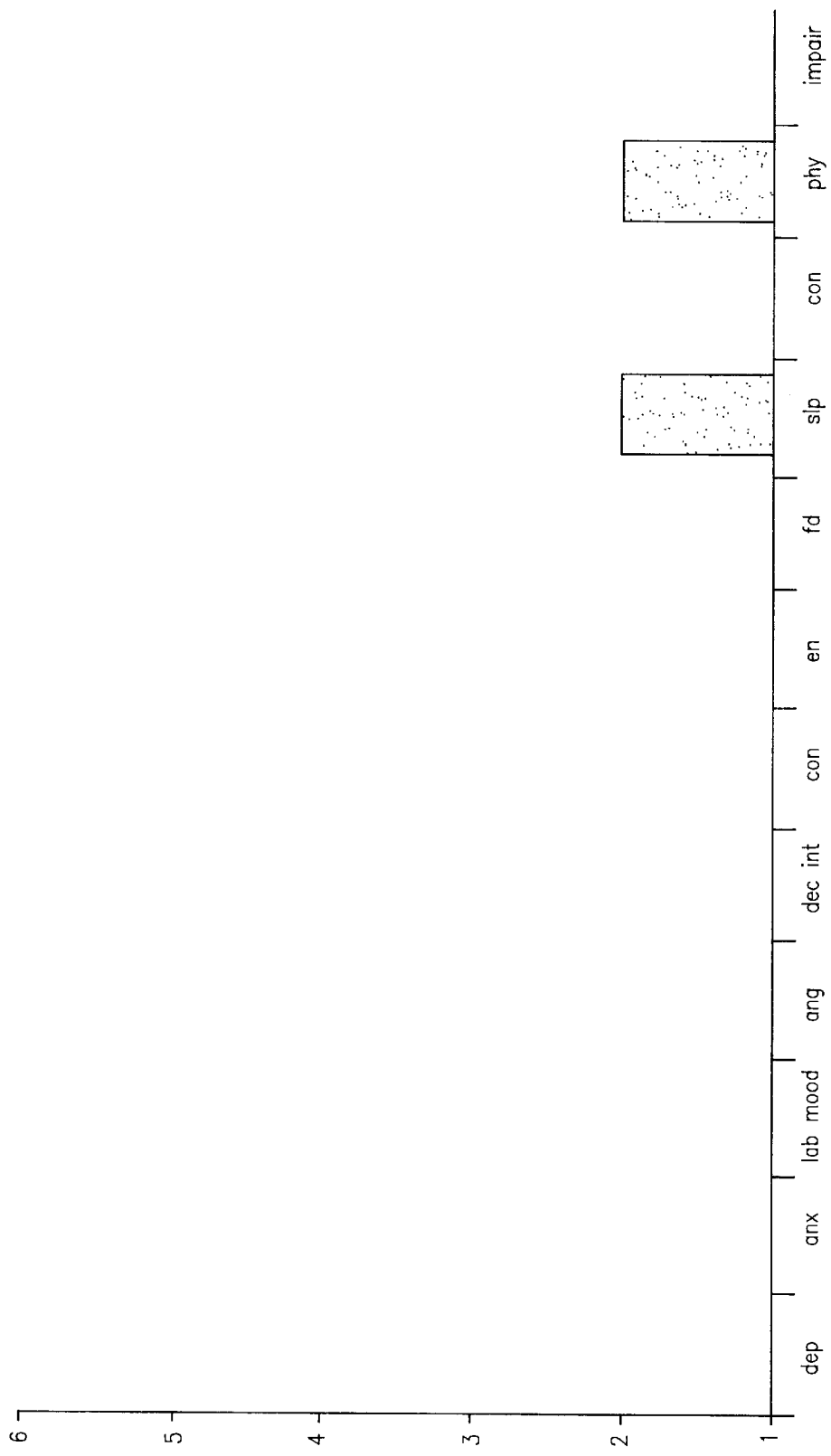
FIG. 8 is a graphical representation of the severity of the symptoms of pre-menstrual syndrome when Patient No. 4 was taking paroxetine and chromium picolinate.

In FIGS. 6–8 the abbreviations for each symptom on the graphs may be translated as follows:

dep=depression anx=anxiety lab mood=mood swings ang=anger dec int=decreased interest in activities con=difficulty in concentrating en=lack of energy, fatigue fd=food cravings slp=sleep disturbance con=loss of control phy=physical symptoms (i.e., breast swelling)

impair =impaired in work, school, relationships

Patient No. 4's formal diagnoses were multiple personality disorder, obsessive-compulsive disorder, major depression disorder, alcoholism (recovering), and pre-menstrual syndrome (PMS).

Set forth below in Table 1 are the research criteria set forth in the *Diagnostic and Statistical Manual of Mental Disorders,* Forth edition, published by the American Psychiatric Association for Pre-Menstrual Dysphoric Disorder, or Pre-Menstrual Syndrome.

TABLE 1

| Research Criteria for Pre-Menstrual Dysphoric Disorder |
|---|
| A. In most menstrual cycles during the past year, five (or more) of the following symptoms were present for most of the time during the last week of the luteal phase, began to remit within a few days after the onset of the follicular phase, and were absent in the week postmenses, with at least one of the symptoms being either (1), (2), (3) or (4): |
|    (1) markedly depressed mood, feelings of hopelessness, or self-deprecating thoughts; |
|    (2) marked anxiety, tension, feelings of being "keyed up," or "on edge"; |
|    (3) marked affective lability (e.g., feeling suddenly sad or tearful or increased sensitivity to rejection); |
|    (4) persistent and marked anger or irritability or increased interpersonal conflicts; |
|    (5) decreased interest in usual activities (e.g., work, school, friends, hobbies); |

TABLE 1-continued

Research Criteria for Pre-Menstrual Dysphoric Disorder (6)    subjective sense of difficulty in concentrating;
    (7)    lethargy, easy fatigability, or marked lack of energy;
    (8)    marked change in appetite, overeating, or specific food cravings;
    (9)    hypersomnia or insomnia;
    (10)   a subjective sense of being overwhelmed or out of control;
    (11)   other physical symptoms, such as breast tenderness or swelling, headaches, joint or muscle pain, a sensation of "bloating," weight gain.
B.    The disturbance markedly interferes with work or school or with usual social activities and relationships with others (e.g., avoidance of social activities, decreased productivity and decreased efficiency at work or school.)
C.    The disturbance is not merely an exacerbation of the symptoms of another disorder, such as Major Depressive Disorder, Panic Disorder, Dysthymic Disorder, or a Personality Disorder (although it may be superimposed on any of these disorders.)
D.    Criteria A, B and C must be confirmed by prospective daily ratings during at least two consecutive symptomatic cycles. (The diagnosis may be made provisionally prior to this confirmation).

Note: In menstruating females, the luteal phase corresponds to the period between ovulation and the onset of menses, and the follicular phase begins with menses. In non-menstruating females (e.g., those who have had a hysterectomy), the timing of luteal and follicular phases may require measurement of circulating reproductive hormones.

Patient No. 4 had a history of severe PMS that started when she was 30 years old. She described a typical menses as follows. She was usually moderately to severely depressed for at least two days during the week before her menses. She had sudden mood swings. One moment she would be crying and the next she would be laughing wildly, or she would have sudden outbursts of anger. She was markedly tense and would fidget constantly. She tired easily and lacked energy. She could barely drag herself out of bed each morning. She craved carbohydrates and often would eat several doughnuts, whole cakes, or boxes of cookies. She slept little, and for two or three nights she would have night sweats that drenched her bed. She also experienced back cramps, bloating and pains in her joints and muscles. She had trouble concentrating and was unable to do life's simplest chores. Her PMS interfered with her ability to function. She lost interest in her favorite hobby, reading.

She was prescribed paroxetine because of its documented efficacy in the treatment of obsessive-compulsive disorder. Patient No. 4 also noticed that it reduced the severity of her symptoms of PMS from severe to moderately severe. The chart in FIG. 6 depicts patient No. 4's rating of her late luteal phase symptoms during a month. During this month, she was taking paroxetine 20 mg t.i.d. and 300 mg of lithium t.i.d. She described this as typical of the menstrual cycles she has while taking paroxetine. Paroxetine decreased the severity of her symptoms but did not eliminate them. It had little to no effect on her energy level, carbohydrate craving and other physical symptoms.

Due to a gastrointestinal disturbance that lasted approximately six weeks, patient No. 4 was unable to take the paroxetine and lithium combination as described above for approximately three weeks. Her "black" depression returned and she frequently thought of suicide. While off paroxetine and lithium, her PMS was severe. It reminded her of the menses she had experienced before she started paroxetine. FIG. 7 depicts patient No. 4's rating of her symptoms of pre-menstrual symptoms during the late luteal phase of her menstrual cycle wherein she had not taken any of the medication in three weeks. This depicts that this menses was one of the more severe ones that she had experienced and was typical of her menses before taking paroxetine.

After her gastrointestinal symptoms subsided, she was left weak, frail, dizzy, depressed and crippled by hand-washing and other rituals that characterized her obsessive-compulsive disorder. She resumed lithium 300 mg t.i.d. and paroxetine 40 mg per day, but her depression was refractory. The inventor then suggested that she begin taking chromium picolinate. At the time of the suggestion, her plasma contained no detectable chromium.

About a week later, she started taking chromium picolinate at a dosage providing 200 µg of chromium twice a day. She started taking chromium picolinate in this amount on the fourth day of menstruation. Thus, she would expect her pre-menstrual syndrome to begin approximately two weeks after beginning to take chromium picolinate.

However, she was not aware of any of the symptoms of pre-menstrual syndrome (except for breast swelling). She was surprised at the onset of menses. For the first time in her recent memory, she was completely without signs or symptoms of PMS, except for breast swelling. Though she experienced breast swelling, she did not experience breast tenderness. The chart presented in FIG. 8 depicts patient No. 4's rating of her symptoms of PMS while taking paroxetine 20 mg t.i.d., lithium 300 mg t.i.d., and chromium picolinate providing 200 µg of chromium b.i.d. Her only symptoms were a slight sleep disturbance and breast swelling. Patient No. 4 noted that this was the least troublesome menses that she had experienced in 15 years.

Thus, an aspect of the present invention includes the treatment of pre-menstrual syndrome (PMS) comprising administering chromium in a preferred dose of 200 µg b.i.d. to a patient in need thereof. Additionally, as paroxetine is a selective serotonin reuptake inhibitor and an antidepressant, it is an aspect of this invention to improve the effectiveness in administering such a composition for the treatment of pre-menstrual syndrome.

Therefore, the present invention relates to a treatment of depression in men and women and to a treatment of pre-menstrual syndrome (PMS) in women using chromium, in a preferred form of chromium picolinate, alone or in conjunction with an antidepressant composition, such as a selective serotonin reuptake inhibitor (SSRI). Chromium potentiates the action of SSRI's and relieves the dysphoria in depression and PMS, reduces or eliminates other symptoms of depression (including craving for carbohydrates, exhaustion and muscle aches), reduces the lag time between administration of SSRI's and clinical response, and reduces the side effects of SSRI's. Further, chromium is neurobiologically active and acts independently of the antidepressant composition, such as an SSRI.

It will be understood that various details of the invention may be changed without departing from the scope of the invention. Furthermore, the foregoing description is for the purpose of illustration only, and not for the purpose of limitation—the invention being defined by the claims.

What is claimed is:

1. A method of improving the effectiveness of a selective serotonin reuptake inhibitor composition as a treatment for pre-menstrual syndrome, comprising administering a composition consisting essentially of a therapeutically effective amount of chromium in a pharmaceutically acceptable form to a patient during a time in which the patient is taking the selective serotonin reuptake inhibitor composition as a treatment for pre-menstrual syndrome.

2. The method according to claim 1 wherein the pharmaceutically acceptable form comprises chromium picolinate.

3. The method according to claim 1 wherein the selective serotonin reuptake inhibitor is selected from the group consisting of sertraline, fluoxetine, paroxetine, fluvoxamine, and combinations thereof.

4. The method according to claim 1 wherein chromium is administered in a dose ranging from about 50 µg to about 1,000 µg daily.

5. The method according to claim 4 wherein chromium is administered in a dose ranging from about 100 µg to about 600 µg daily.

6. The method according to claim 5 wherein chromium is administered in a dose ranging from about 200 µg to about 500 µg daily.

7. The method according to claim 1 wherein the therapeutically effect amount is administered at least once a day.

8. The method according to claim 1 wherein the therapeutically effect amount is administered at least twice a day.

9. The method according to claim 1 wherein the therapeutically effect amount is administered three times a day.

10. A method of improving the effectiveness of a selective serotonin reuptake inhibitor composition as a treatment for pre-menstrual syndrome, comprising administering a composition consisting essentially of a therapeutically effective amount of chromium in a pharmaceutically acceptable form to a patient during a time in which the patient is taking the selective serotonin reuptake inhibitor composition as a treatment for pre-menstrual syndrome, wherein chromium is administered in a dose ranging from about 1 µg to about 10 µg per kilogram body weight of the patient daily.

11. The method according to claim 10, wherein chromium is administered in a dose ranging from about 2 µg to about 8 µg per kilogram body weight of the patient daily.

12. The method according to claim 11, wherein chromium is administered in a dose ranging from about 4.5 µg to about 6 µg per kilogram body weight of the patient daily.

* * * * *